United States Patent [19]

Gardner

[11] Patent Number: 5,447,516
[45] Date of Patent: Sep. 5, 1995

[54] DOUBLE-BLADED SCALPEL

[76] Inventor: Terry B. Gardner, 2158 Wayman St., Shreveport, La. 71118

[21] Appl. No.: 248,447

[22] Filed: May 23, 1994

[51] Int. Cl.$^6$ ............................................. A61B 17/32
[52] U.S. Cl. ........................................ 606/167; 30/304
[58] Field of Search .................... 30/304, 305, 339; 606/166, 167, 170

[56] References Cited

U.S. PATENT DOCUMENTS

| | | | |
|---|---|---|---|
| 1,226,797 | 5/1917 | Newman | 30/304 |
| 1,830,692 | 11/1931 | Becker | 30/304 |
| 2,130,949 | 9/1938 | Collens | 30/304 |
| 2,528,166 | 10/1950 | Orr et al. | 30/304 |
| 3,452,754 | 7/1969 | Stayer . | |
| 3,998,229 | 12/1976 | Barton . | |
| 4,578,865 | 4/1986 | Keller . | |
| 4,969,267 | 11/1990 | Anenberg | 30/304 |
| 5,026,385 | 6/1991 | Schutte et al. . | |
| 5,100,391 | 5/1992 | Schutte et al. . | |

Primary Examiner—Stephen C. Pellegrino
Assistant Examiner—William Lewis
Attorney, Agent, or Firm—John M. Harrison

[57] ABSTRACT

A double-bladed scalpel for cutting tissue sections from a tissue specimen for microscopic examination and the like. In a preferred embodiment the double-bladed scalpel is characterized by a pair of scalpel blades disposed in parallel, substantially coplanar relationship with respect to each other and connected to each other by a connecting element which may be folded such that the cutting margin of each scalpel blade is positioned in parallel, adjacent relationship with respect to the cutting margin of the opposite scalpel blade. One of the scalpel blades is provided with a handle slot for receiving a correspondingly-shaped blade mount protuberance formed on conventional scalpel handles to removably mount the double-bladed scalpel on the scalpel handle.

2 Claims, 1 Drawing Sheet

DOUBLE-BLADED SCALPEL

BACKGROUND OF THE INVENTION

1. Field of the Invention

This invention relates to surgical scalpels having two blades for producing parallel incisions in a tissue and more particularly, to a double-bladed scalpel which may be removably mounted on conventional scalpel handles for producing tissue sections of desired thickness from a tissue specimen. In a preferred embodiment of the invention the double-bladed scalpel is characterized by a pair of scalpel blades which may be shaped in any standard scalpel blade configuration and one disposed in parallel, substantially coplanar relationship with respect to each other and connected to each other by means of a connecting element which is continuous with the upper edge of each blade. The connecting element may be folded such that the cutting margin of each scalpel blade is positioned in parallel, adjacent relationship with respect to the cutting margin of the other scalpel blade. One of the scalpel blades is provided with a handle slot for receiving a conventional blade mount protuberance provided near the end of a conventional scalpel handle to removably mount the double-bladed scalpel on the scalpel handle.

Conventionally, tissue sections are formed from a tissue using a single conventional scalpel or a scalpel characterized by a pair of scalpel blades mounted on a scalpel handle in parallel, adjacent relationship with respect to each other by means of screws and wing nuts. However, use of these scalpels is tedious and time-consuming because the screws and wing nuts must be removed in order to remove the blades from the handle. The double-bladed scalpel of this invention is much more efficient and easier to use than conventional double-bladed scalpels because the disposable, parallel blade unit is shaped from a single plate or blank and can be easily attached or removed from a standard or conventional scalpel handle. Additionally, the distance between the blades may be varied when the blank is bent to cut tissue sections of desired thickness. The thinner tissue sections made possible by the double-bladed scalpel of this invention lend themselves to better fixation and processing than thicker tissue sections typically made by other double-bladed scalpels. Some specific applications which benefit from using thinner tissue sections include cutting cruciate sections for evaluation of surgical resection margins, cutting transmural sections from tubular gastrointestinal organs and other situations in which difficulty arises due to differential tissue movement after a single incision. The double-bladed scalpel of this invention is also safer to use than conventional scalpels because thin cuts can be made in the tissue without requiring the tissue to be held in place by fingers positioned near the cutting blade.

2. Description of the Prior Art

Various knives having two blades for cutting parallel incisions or sections in tissues and other materials, are known in the art. U.S. Pat. No. 3,452,754, dated Jul. 1, 1969, to Anna M. Stayer, describes a "Double Scalpel For Removal of Scar Tissue", characterized by a pair of scalpel blades removably mounted on a handle in spaced, adjacent relationship with respect to each other and having an adjusting mechanism for spacing the scalpel blades various distances apart. U.S. Pat. No. 3,998,229, dated Dec. 21, 1976, to Richard T. Barton, discloses a "Surgical Margin Blade" characterized by a double cutting blade having a center vertical blade which slices a margin of tissue around a surgical site. The blade permits the positive establishment of tumor or disease tissue limits by delineating the margin of normal tissue that is free of tumor or diseased tissue. U.S. Pat. No. 4,578,865, dated Apr. 1, 1986, to Jeffrey Keller, details a "Tile-Cutting Device Having Parallel Blades" for forming a rabbet edge on ceiling tile. Two blades are mounted in parallel relationship with respect to each other, one of which is fixed and the other movable with respect to the fixed blade such that it may extend beyond the fixed blade to produce a deeper cut. U.S. Pat. No. 5,026,385, dated Jun. 25, 1991, to Michael J. Schutte, et al, and U.S. Pat. No. 5,100,391, dated Mar. 31, 1992, also to Michael J. Schutte, et al, both describe a "Double-Bladed Scalpel" for removing tissues requiring consistent width along their length. A pair of identical metal scalpel blades are embedded in an integral rigid supporting handle and protrude outwardly from respective bifurcations of a bifurcated handle end. A contoured finger rest shaped in the handle permits the user to exert substantial cutting pressure on the scalpel blades, such as when scribing of bony tissue is required.

It is an object of this invention to provide a folded double-bladed scalpel for removably mounting on conventional or specially designed scalpel handles to form parallel incisions in tissue or other material.

Another object of this invention is to provide a disposable double-bladed scalpel shaped from a single plate or blank and foldable for removably mounting on conventional scalpel handles to cut tissue sections of desired thickness from a tissue specimen.

Yet another object of this invention is to provide a disposable or autoclavable double-bladed scalpel characterized by a first scalpel blade disposed in spaced, parallel, substantially coplanar relationship with respect to a second scalpel blade in a scalpel blank and having an upper margin connected to the upper margin of the second scalpel blade by means of a connecting element which may be folded longitudinally such that the cutting margin of the first scalpel blade is located in parallel, adjacent, selectively spaced relationship with respect to the cutting margin of the second scalpel blade to facilitate cutting tissue sections from a tissue specimen, the thickness of which tissue section is equal to the distance between the cutting margin of the first blade and the cutting margin of the second blade.

SUMMARY OF THE INVENTION

These and other objects of the invention are provided in a disposable or sterilizable double-bladed scalpel for removable attachment to a conventional or specially designed scalpel handle to cut tissue sections of selected thickness from a tissue specimen, which double-bladed scalpel is characterized by a scalpel blank having a first scalpel blade extending from an adjacent, parallel, selectively spaced second scalpel blade by means of a connecting element which is continuous with the upper margin of the first scalpel blade and the upper margin of the second scalpel blade. The connecting element of the scalpel blank is folded or bent such that the cutting margin of the first scalpel blade is positioned a selected distance from the cutting margin of the parallel second scalpel blade to produce a tissue section of corresponding thickness. The first scalpel blade includes a handle slot for receiving a conventional, correspondingly-shaped blade mount protuberance formed on the end of a conventional scalpel handle to removably mount the double-bladed scalpel oh the handle.

BRIEF DESCRIPTION OF THE DRAWINGS

The invention will be better understood by reference to the accompanying drawing, wherein.

DESCRIPTION OF THE PREFERRED EMBODIMENTS

Figure 2:
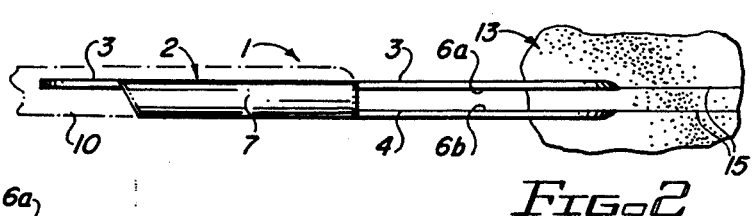
FIG. 2 is a top view of the double-bladed scalpel illustrated in FIG. 1, mounted on a scalpel handle and more particularly detailing a preferred technique for using the double-bladed scalpel to form parallel incisions in a tissue specimen.
Figure 3:
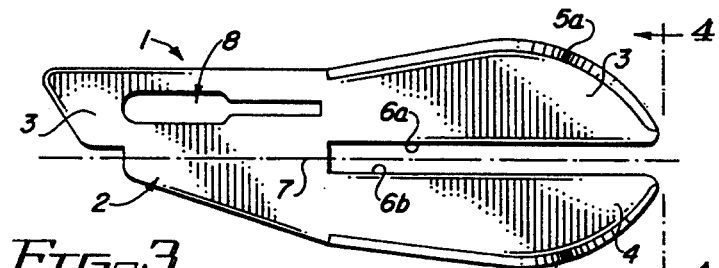
FIG. 3 is a top view of the double-bladed scalpel, illustrated in blank, unfolded configuration.

Referring initially to FIGS. 1-6 of the drawing, in a first preferred embodiment the double-bladed scalpel of this invention is generally illustrated by reference numeral 1. The double-bladed scalpel 1 is characterized by a flat dual scalpel blank 2, including a first blade 3, typically constructed of stainless steel or blue tempered surgical steel and having a longitudinal first connecting margin 6a and a curved first cutting margin 5a, spaced from the first connecting margin 6a, as illustrated in FIG. 3. The dual scalpel blank 2 also includes a similar second blade 4, disposed in substantially coplanar relationship with respect to the first blade 3 and including a curved second cutting margin 5b and a second connecting margin 6b located in spaced, parallel relationship with respect to the first connecting margin 6a. The first connecting margin 6a is connected to the second connecting margin 6b by means of a connecting element 7, which terminates the first connecting margin 6a and second connecting margin 6b. A conventional handle slot 8 is provided in the rearwardly-extending segment of the first blade 3 for removably receiving a conventional blade mount protuberance (not illustrated) provided on a conventional scalpel handle 10 (illustrated in phantom in FIGS. 2 and 11) to removably and conventionally mount the folded dual scalpel blank 2 on the scalpel handle 10.

Figure 1:
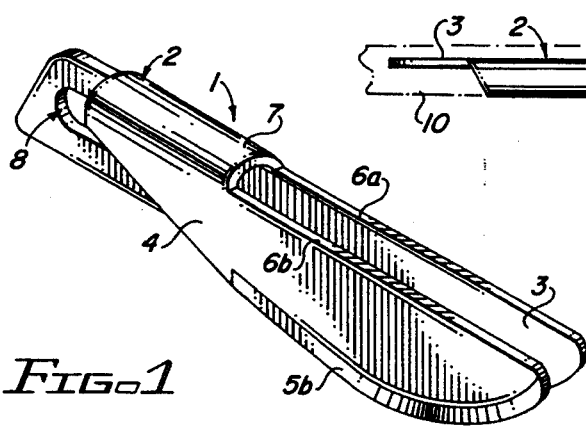
FIG. 1 is a perspective view of a first preferred embodiment of the double-bladed scalpel of this invention, illustrated in folded, functional configuration.
Figure 4:
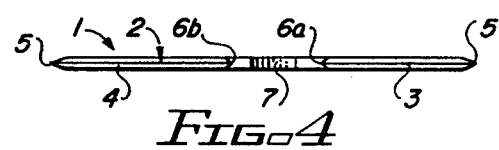
FIG. 4 is a front view of the unfolded double-bladed scalpel in blank, taken along section line 4—4 in FIG. 3.
Figure 6:
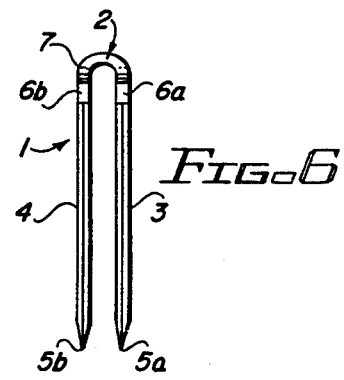
FIG. 6 is a front view of the folded double-bladed scalpel, taken along section line 6—6 in FIG. 5.
Figure 5:
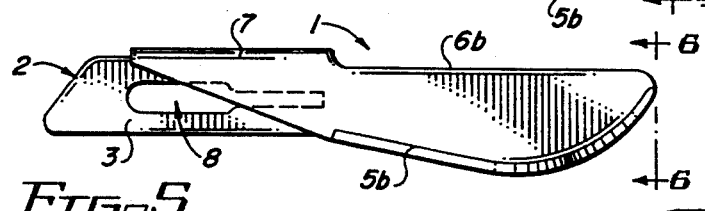
FIG. 5 is a side view of the folded double-bladed scalpel illustrated in FIG. 1.
Figure 8:
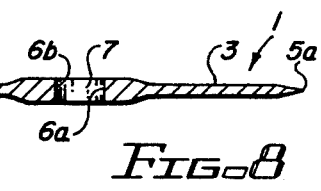
FIG. 8 is a sectional view of the unfolded double-bladed scalpel in blank, taken along section line 8—8 in FIG. 7.

In typical application, the dual scalpel blank 2 is bent or folded on a suitable jig from a single blank having the configuration illustrated in FIG. 3 to the functional configuration shown in FIG. 1 at a selected blade spacing. Accordingly, the first connecting margin 6a and second connecting margin 6b are unitary with the first blade 3 and second blade 4. The double bladed scalpel 1 is then conventionally first mounted on the scalpel handle 10 (as described above) and the connecting element 7 facilitates location of the first cutting margin 5a in the selected spaced, parallel, adjacent relationship with respect to the second cutting margin 5b, as illustrated in FIGS. 1 and 6. The double bladed scalpel 1 may then be used to form parallel incisions 15 in a tissue specimen 13 in order to obtain tissue sections (not illustrated) from the tissue specimen 13, for example, as illustrated in FIG. 2.

Figure 7:
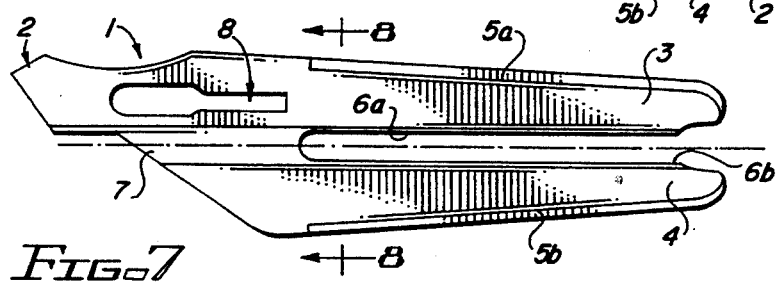
FIG. 7 is a top view of another preferred embodiment of the double-bladed scalpel of this invention, illustrated in blank, unfolded configuration.
Figure 10:
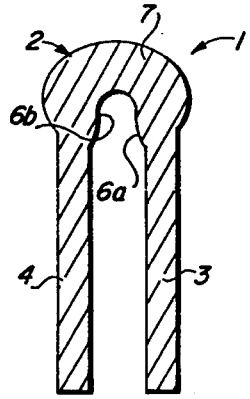
FIG. 10 is a sectional view of the folded double-bladed scalpel, taken along section line 10—10 in FIG. 9.
Figure 9:
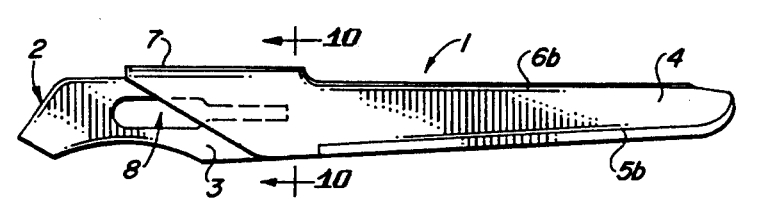
FIG. 9 is a side view of the double-bladed scalpel, illustrated in folded configuration.
Figure 11:
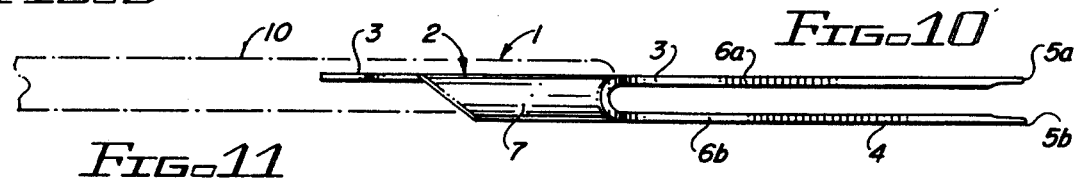
FIG. 11 is a top view of the folded double-bladed scalpel illustrated in FIG. 9.

Referring next to FIGS. 7-11 of the drawings, in a second preferred embodiment of the invention the dual scalpel blank 2 of the double-bladed scalpel 1 includes an elongated first blade 3 having a straight first cutting margin 5a and a first connecting margin 6a. A similar, elongated second blade 4 having a straight second cutting margin 5b and a second connecting margin 6b extends from the first blade 3 by means of a connecting element 7, as illustrated in FIG. 7 and as described above with respect to the first embodiment herein illustrated in FIGS. 1-6. As illustrated in FIG. 11, the dual scalpel blade 2 is conventionally removably mounted on a scalpel handle 10 in the same manner as described above with respect to the first embodiment illustrated in FIGS. 1-6. Since each blade is elongated, the first connecting margin 6a and second connecting margin 6b are preferably each characterized by a thickened margin which tapers to the first cutting margin 5a, and second cutting margin 5b, respectively, at the ends thereof, as illustrated in FIGS. 9 and 11, for reinforcing the corresponding first blade 3 and second blade 4 to prevent the blades from bending as pressure is applied to the scalpel handle 10 to obtain sections of the tissue specimen 13, as illustrated in FIG. 2.

It will be appreciated by those skilled in the art that the first blade 3 and second blade 4 of the double bladed scalpel 1 may be shaped in virtually any desired size and shape and may be adapted to fit any desired handle to facilitate cutting tissue sections or surgical resections of any type. Referring again to FIGS. 3 and 7 of the drawing, it is understood that the handle slot 8 may be omitted from the first blade 3 and replaced with a pair of spaced, threaded bolt openings (not illustrated) for receiving respective mount bolts (not illustrated) which are threaded in the scalpel handle 10 to removably seat the dual scalpel blade 2 on the scalpel handle 10. Furthermore, the respective dual scalpel blanks 2 may be stamped or otherwise constructed from surgical metal stock according to the knowledge of those skilled in the art.

Accordingly, while the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A double scalpel blade for removably mounting on a scalpel handle having a single blade mount protuberance to facilitate cutting uniform tissue sections of selected depth from a tissue specimen, said double scalpel blade comprising an elongated, flat first blade having a curvilinear first cutting margin distal to the handle and a straight first connecting margin spaced from said first cutting margin; an elongated second blade disposed in parallel relationship with respect to said first blade, said second blade having a curvilinear second cutting margin distal to the handle and a straight second connecting margin spaced from said second cutting margin, said second connecting margin disposed in spaced, parallel relationship with respect to said first connecting margin and said second cutting margin disposed in spaced, parallel relationship with respect to said first cutting margin to define a space of uniform width between said first blade and said second blade; a unitary connecting member linearly continuous with said first connecting margin and said second connecting margin for connecting said first blade to said second blade; and a single mount slot provided in said first blade proximal to said handle for receiving the blade mount protuberance on the scalpel handle and removably mounting said first blade on the handle, whereby said connecting member positions said first blade in parallel, selectively spaced relationship with respect to said second blade.

2. A double scalpel blade for removably mounting on a scalpel handle having a blade mount protuberance, said double scalpel blade comprising an elongated, flat first blade having a substantially straight first cutting margin distal to the handle; an elongated, flat second blade having a substantially straight second cutting margin distal to the handle; a unitary connecting member linearly continuous with said first blade for connecting said first blade to said second blade; and a single mount slot provided in said unitary connecting member, said mount slot positioned proximal to the handle for receiving the blade mount protuberance on the scalpel handle and removably mounting said first blade and said second blade on the handle, whereby said unitary connecting member is folded along an axis extending through said unitary connecting member in parallel relationship with respect to the longitudinal axis of said first blade and said second blade to position said first blade in parallel relationship with respect to said second blade and define an unobstructed space of equal width between said first blade and said second blade co-extensive with said cutting margins.

* * * * *